(12) United States Patent
Thomas et al.

(10) Patent No.: US 11,010,556 B1
(45) Date of Patent: *May 18, 2021

(54) CONVERSATIONAL AGENT

(71) Applicant: Allscripts Software, LLC, Chicago, IL (US)

(72) Inventors: Matthew Dreselly Thomas, Atlanta, GA (US); William Loftus, Roswell, GA (US); Harry Wepuri, Atlanta, GA (US); Arif Ogan, Atlanta, GA (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 420 days.

This patent is subject to a terminal disclaimer.

(21) Appl. No.: 15/961,585

(22) Filed: Apr. 24, 2018

Related U.S. Application Data

(63) Continuation of application No. 14/278,828, filed on May 15, 2014, now Pat. No. 10,002,130.

(60) Provisional application No. 61/823,901, filed on May 15, 2013.

(51) Int. Cl.
*G06F 16/00* (2019.01)
*G06F 40/295* (2020.01)
*G06F 19/00* (2018.01)
*G06F 40/35* (2020.01)

(52) U.S. Cl.
CPC ............ *G06F 40/295* (2020.01); *G06F 19/00* (2013.01); *G06F 40/35* (2020.01)

(58) Field of Classification Search
CPC ...... G06F 3/167; G06F 40/58; G06F 16/9535; G06F 8/61; G06F 8/65
IPC ........................................................ G06F 16/00
See application file for complete search history.

(56) References Cited

U.S. PATENT DOCUMENTS

| 2009/0177477 | A1* | 7/2009 | Nenov ............... G16H 10/60 704/275 |
| 2011/0161077 | A1* | 6/2011 | Bielby ................. G10L 15/32 704/231 |
| 2011/0258049 | A1* | 10/2011 | Ramer .............. G06Q 30/0273 705/14.66 |
| 2011/0276895 | A1* | 11/2011 | van der Flier ........ G06F 3/0481 715/751 |

* cited by examiner

*Primary Examiner* — Yicun Wu
(74) *Attorney, Agent, or Firm* — Loza & Loza, LLP; Peter Zura

(57) ABSTRACT

A method includes converting a user's utterance to text; encapsulating the converted text in a rheme object; searching, for each of a plurality of topics, for keywords in the converted text; determining a relevancy metric for each of the plurality of topics based on such searching; selecting one or more topics based on determined relevancy metrics; comparing some or all of the converted text to names in one or more patient lists or databases; identifying a unique patient whose name is contained in the converted; attaching an indication of the identified patient to the rheme object; effecting an action based on the selected one or more topics and the attached patient indication; and saving the topic in a conversation history with a reference to the identified patient.

9 Claims, 17 Drawing Sheets

User: "Show me all results for Peter Eastman"

Computer: "Okay, here are all results for Peter N. Eastman"

User: "How about just the abnormal results"

Computer: "Okay, here are all abnormal results for Peter N. Eastman"

User: "Now how about for Sally Smith"

Computer: "I've found the following visits with a similar name to Sally Smith. Which one did you mean?"

Computer: "Okay, here are all abnormal results for Sally Ann Smith"

User: "Show me allergies"

Computer: "For which patient would you like to view allergies?"

CONVERSATIONAL AGENT

RELATED APPLICATIONS

The present applications claims priority to U.S. patent application Ser. No. 14/278,828 to Thomas, et al., titled "Conversational Agent", filed May 15, 2014, which claims priority to Provisional Patent Application No. 61/823,901, the contents of each being incorporated by reference in their entireties herein.

CROSS-REFERENCE TO RELATED APPLICATION

The present application is a continuing application of Ser. No. 14/278,828, filed May 15, 2014 which '828 application is a nonprovisional patent application of 61/823,901, filed May 15, 2013. The present application incorporates by reference each of these priority applications and the Appendix attached hereto.

COPYRIGHT STATEMENT

All of the material in this patent document, including the computer program listing, is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

COMPUTER PROGRAM LISTING

Submitted concurrently herewith via the USPTO's electronic filing system, and incorporated herein by reference, are computer program files including instructions, routines, and/or other contents of several computer program. A table setting forth the name and size of files included in the computer program listing is included below.

| File Name | Creation Date | File Size (bytes) |
| --- | --- | --- |
| readme.txt | May 14, 2014 14:57 | 2745 |
| ASCIFY.txt | May 14, 2014 14:57 | 37473 |
| MDS.1XT | May 14, 2014 14:57 | 952032 |

One of these files. "readme.txt", contains instructions for extracting information from "MDS.TXT". This file is a compressed binary file that has been converted to ascii format. This file can be converted back to a compressed .zip archive utilizing an assembly conversion program source code for which is contained in "ascify.txt". The readme file includes instructions for compiling and running this conversion program, and instructions for converting the other text file to a compressed, binary files.

Some of these compressed, binary files include source code written in C. The target environment for implementations utilizing such source code is 32-bit or 64-Windows XP, Vista, or 7.

BACKGROUND OF THE INVENTION

The present invention generally relates to medical software and systems and methodologies for interfacing with medical software.

Interacting with medical software conventionally requires that a user utilize an input device such as a mouse, keyboard, or touchscreen. User input via such devices can be useful, but can at times be impractical, slow, or inefficient.

The use of voice as an input for software is known in other contexts. For example, Apple's "Siri" is an intelligent personal assistant which performs tasks or otherwise responds to natural language.

A need exists for improvement in medical software and systems and methodologies for interfacing with medical software. This and other needs are addressed by one or more aspects of the present invention.

SUMMARY OF THE INVENTION

The present invention includes many aspects and features. Moreover, while many aspects and features relate to, and are described in, the context of health care, the present invention is not limited to use only in this context, as will become apparent from the following summaries and detailed descriptions of aspects, features, and one or more embodiments of the present invention.

Accordingly, one aspect of the present invention relates to software implementing a conversational agent.

Another aspect relates to a method which includes converting a user's utterance to text; encapsulating the converted text in a rheme object; searching, for each of a plurality of topics, for keywords in the converted text; determining a relevancy metric for each of the plurality of topics based on such searching; selecting one or more topics based on determined relevancy metrics; comparing some or all of the converted text to names in one or more patient lists or databases; identifying a unique patient whose name is contained in the converted; attaching an indication of the identified patient to the rheme object; effecting an action based on the selected one or more topics and the attached patient indication; and saving the topic in a conversation history with a reference to the identified patient.

Another aspect relates to a method comprising receiving, from a user of an electronic device via a microphone of the electronic device, a first utterance corresponding to a first spoken command, the first spoken command identifying a first patient; converting, utilizing one or more processors, the first utterance to first text; encapsulating, utilizing one or more processors, the converted first text in a first rheme object; searching, for each of a plurality of topics utilizing one or more processors, for keywords in the converted first text; determining, utilizing one or more processors, a relevancy metric for each of the plurality of topics based on the keyword searching of the converted first text; selecting, utilizing one or more processors, one or more topics as a first set of one or more relevant topics based on the determined relevancy metrics; comparing, utilizing one or more processors, some or all of the converted first text to names in one or more patient lists or databases; determining, utilizing one or more processors based on comparing some or all of the converted first text, that the first utterance included an identification of the first patient; attaching, utilizing one or more processors, an indication of the identified first patient to the rheme object; displaying, to the user via a display device associated with the electronic device, first information associated with the first patient based on the selected first set of one or more relevant topics and the identified first patient; saving, utilizing one or more processors, the selected first set of one or more relevant topics in a conversation history in association with the identified first patient; receiving, from the user of the electronic device via the microphone of the electronic device, a second utterance corresponding to a second spoken command, the second spoken command not including an identification of a patient; converting, utilizing one or more processors, the second utterance to second text; encapsulating, utilizing one or more processors, the converted second text in a second rheme object; searching, for each of a plurality of topics utilizing one or more processors, for keywords in the converted second text; determining, utilizing one or more processors, a relevancy metric for each of the plurality of topics based on the keyword searching of the converted second text; selecting, utilizing one or more processors, one or more topics as a second set of one or more relevant topics based on the determined relevancy metrics; comparing, utilizing one or more processors, some or all of the converted second text to names in the one or more patient lists or databases; determining, utilizing one or more processors based on comparing some or all of the converted second text, that the second utterance did not include an identification of a patient, and, based thereon, attaching an indication of the previously identified first patient to the rheme object; displaying, to the user via the display device associated with the electronic device, second information associated with the first patient based on the selected second set of one or more relevant topics and the previous identification of the first patient; and saving, utilizing one or more processors, the selected second set of one or more relevant topics in a conversation history in association with the previously identified first patient.

In one or more preferred implementations, the method further includes receiving, from the user of the electronic device via the microphone of the electronic device, a third utterance corresponding to a third spoken command, the third spoken command identifying a second patient; converting, utilizing one or more processors, the third utterance to third text; encapsulating, utilizing one or more processors, the converted third text in a third rheme object; searching, for each of a plurality of topics utilizing one or more processors, for keywords in the converted third text; determining, utilizing one or more processors, a relevancy metric for each of the plurality of topics based on the keyword searching of the converted third text; selecting, utilizing one or more processors, one or more topics as a third set of one or more relevant topics based on the determined relevancy metrics; comparing, utilizing one or more processors, some or all of the converted third text to names in one or more patient lists or databases; determining, utilizing one or more processors based on comparing some or all of the converted third text, that the third utterance included an identification of the second patient; attaching, utilizing one or more processors, an indication of the identified second patient to the rheme object; displaying, to the user via the display device associated with the electronic device, third information associated with the second patient based on the selected third set of one or more relevant topics and the identified second patient; and saving, utilizing one or more processors, the selected third set of one or more relevant topics in a conversation history in association with the identified second patient. Additionally, in some preferred implementations, the method further includes receiving, from the user of the electronic device via the microphone of the electronic device, a fourth utterance corresponding to a fourth spoken command, the fourth spoken command not including an identification of a patient; converting, utilizing one or more processors, the fourth utterance to fourth text; encapsulating, utilizing one or more processors, the converted fourth text in a fourth rheme object; searching, for each of a plurality of topics utilizing one or more processors, for keywords in the converted fourth text; determining, utilizing one or more processors, a relevancy metric for each of the plurality of topics based on the keyword searching of the converted fourth text; selecting, utilizing one or more processors, one or more topics as a fourth set of one or more relevant topics based on the determined relevancy metrics; comparing, utilizing one or more processors, some or all of the converted fourth text to names in the one or more patient lists or databases; determining, utilizing one or more processors based on comparing some or all of the converted fourth text, that the fourth utterance did not include an identification of a patient, and, based thereon, attaching an indication of the previously identified second patient to the rheme object; displaying, to the user via the display device associated with the electronic device, fourth information associated with the second patient based on the selected fourth set of one or more relevant topics and the previous identification of the second patient; and saving, utilizing one or more processors, the selected fourth set of one or more relevant topics in a conversation history in association with the previously identified second patient.

In one or more preferred implementations, the electronic device comprises a mobile device.

In one or more preferred implementations, the electronic device comprises a tablet.

In one or more preferred implementations, the electronic device comprises a phone.

In one or more preferred implementations, the electronic device comprises a laptop.

In one or more preferred implementations, the electronic device comprises a desktop.

In one or more preferred implementations, the display device associated with the electronic device comprises a touchscreen.

In one or more preferred implementations, the display device associated with the electronic device comprises a monitor.

In one or more preferred implementations, the display device associated with the electronic device comprises a television.

In one or more preferred implementations, converting, utilizing one or more processors, the first utterance to first text is performed at the electronic device.

In one or more preferred implementations, converting, utilizing one or more processors, the first utterance to first text is performed remote from the electronic device.

In one or more preferred implementations, converting, utilizing one or more processors, the first utterance to first text is performed at a first server remote from the electronic device. Further, in some implementations, encapsulating, utilizing one or more processors, the converted first text in a first heme object is performed at the first server. On the other hand, in some implementations, encapsulating, utilizing one or more processors, the converted first text in a first rheme object is performed at a second server.

In one or more preferred implementations, displaying first information associated with the first patient comprises displaying results associated with the first patient.

In one or more preferred implementations, each of the determined relevancy metrics comprises a numerical score.

Another aspect relates to a method which includes receiving, from a user of an electronic device via a microphone of the electronic device, an utterance corresponding to a spoken command, the spoken command identifying a first patient; converting, utilizing one or more processors, the utterance to text; encapsulating, utilizing one or more processors, the converted text in a rheme object; searching, for each of a plurality of topics utilizing one or more processors, for keywords in the converted text; determining, utilizing one or more processors, a relevancy metric for each of the plurality of topics based on the keyword searching; selecting, utilizing one or more processors, one or more topics as one or more relevant topics based on the determined relevancy metrics; comparing, utilizing one or more processors, some or all of the converted text to names in one or more patient lists or databases; determining, based on such comparing, that the utterance included an identification of the first patient; attaching, utilizing one or more processors, an indication of the identified first patient to the rheme object; displaying, to the user via a display device associated with the electronic device, information associated with the first patient based on the selected one or more topics and the identified first patient; and saving, utilizing one or more processors, the selected one or more topics in a conversation history in association with the identified first patient.

Another aspect relates to a method which includes receiving, from a user of an electronic device via a microphone of the electronic device, an utterance corresponding to a spoken command, the spoken command identifying a first patient; converting, utilizing one or more processors, the utterance to text; encapsulating, utilizing one or more processors, the converted text in a rheme object; searching, for each of a plurality of topics utilizing one or more processors, for keywords in the converted text; determining, utilizing one or more processors, a relevancy metric for each of the plurality of topics based on the keyword searching; selecting, utilizing one or more processors, one or more topics as one or more relevant topics based on the determined relevancy metrics; comparing, utilizing one or more processors, some or all of the converted text to names in one or more patient lists or databases; determining, based on such comparing, that the utterance included an identification of the first patient; attaching, utilizing one or more processors, an indication of the identified first patient to the rheme object; effecting, utilizing one or more processors, an action based on the selected one or more topics and the identified first patient; and saving, utilizing one or more processors, the selected one or more topics in a conversation history in association with the identified first patient.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
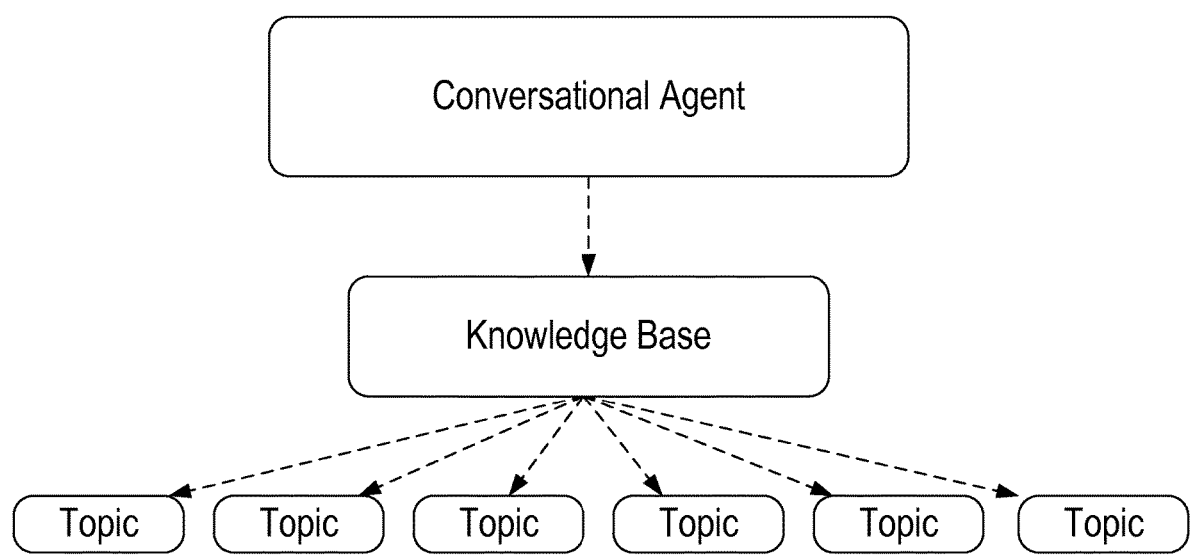
FIG. 1 illustrates topics corresponding to a conversational agent.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers" "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers." as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

One or more preferred embodiments relate to a patient-centric conversational agent that allows physicians to quickly access patient records using a natural language speech interface.

Such a conversational agent (CA), or dialogue system, is a computer system that a user can communicate with to access data. In a preferred implementation, the conversational agent uses both touch and speech as input channels, while using both a graphical display and audio as output channels. The workflow preferably follows the conventions of a typical human-to-human conversation, in that each participant in the conversation takes turns speaking. The conversational agent preferably keeps track of its history of topics and the related patients.

In preferred implementations, the conversational agent uses knowledge of pragmatics to facilitate intuitive interaction. For example, physicians can request data about a patient mentioned in a previous statement (e.g., "How about orders for that patient?"). Additionally, physicians need not drill-down or drill-up to navigate patient data. Instead, they may go directly to specific patient data from anywhere. For example, a clinician may say "Show me results for Sally Smith", followed immediately by "I'd like to cancel an order for Ronald Klein". These two actions might take a significantly longer time to access via conventional input methodologies, such as, for example, touch.

In a preferred implementation, a patient-centric conversational agent utilizes a set of topics, as illustrated in FIG. 1. Topics represent actions that the conversational agent is able to perform at the request of the user (e.g. Display results, Discontinue Orders, Change Patient Notifications, etc). In some implementations, topics can be characterized as the equivalent to "user-stories".

Preferably, when a user utters a phrase, the words are first converted to text by a speech recognition system (such as, for example, Nuance or M*Modal). The resulting text is encapsulated in an object, called a rheme, for further processing by the conversational agent. Each topic in the topic-set then has the opportunity to search for certain keywords in the text phrase. Topics are chosen using a metric "relevancy" which is a function of the number of keywords a given topic finds in transcribed text.

Figure 2:
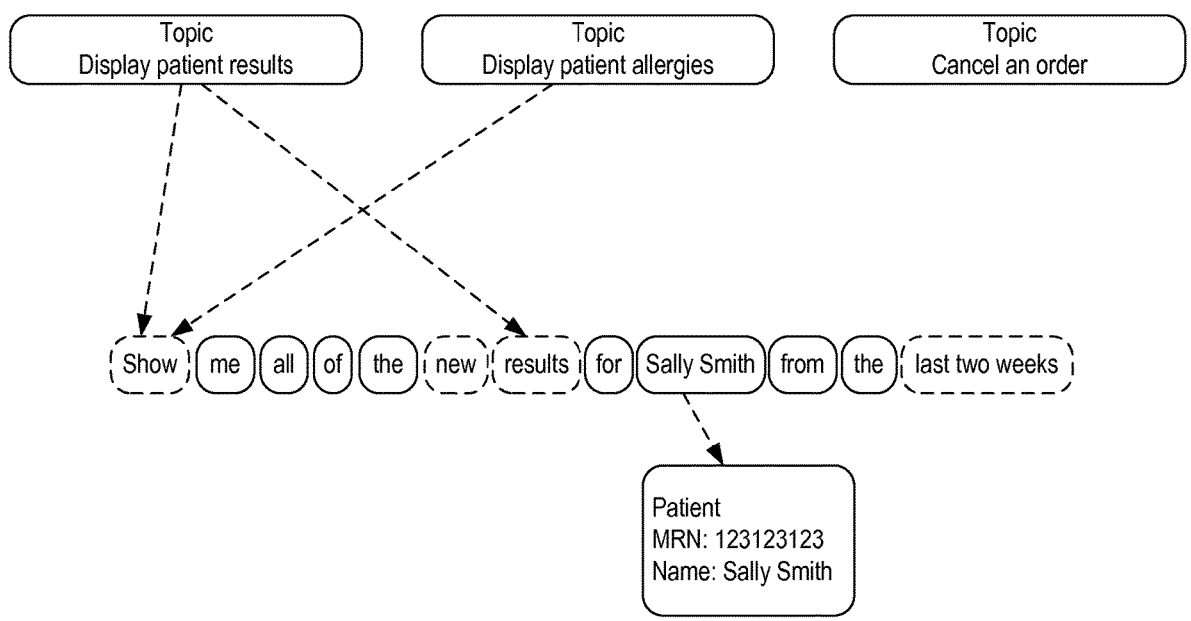
FIG. 2 provides an exemplary illustration of processing of transcribed text.

FIG. 2 provides an exemplary illustration of processing of the transcribed text "Show me all of the new results for Sally Smith from the last two weeks". The phrases "Show", "new", "results", and "last two weeks" are highlighted as having significance to one or more topics. The arrowed lines illustrate, for several exemplary topics, any words which have significance to that topic. The relevancy score for each topic is based on the number of words that are found in the transcribed text that have significance to that particular topic. In the illustrated example, the topic "Display patient results" would be found to be relevant and display of such results would be effected. Notably, in one or more preferred implementations, words or phrases can be found to trigger filters for various topics. For example, the word "new" might cause only new results to be displayed in connection with a "Display patient results" topic.

Additionally, the text phrase is searched by the conversational agent for any name on a patient list or in a patient database. For example, for the transcribed text in FIG. 2, the phrase "Sally Smith" has been identified as representing the name of a patient. When a name is found, an identification of that patient is attached the rheme object.

In one or more preferred implementations, a conversational agent uses an emergent architecture and a connectionist approach that allows any number of patient-centric topics to be added to the agent. In one or more preferred implementations, there are forty or more specialized topics in use, with each having a basic purpose that a connectionist approach is able to handle.

Figure 3:
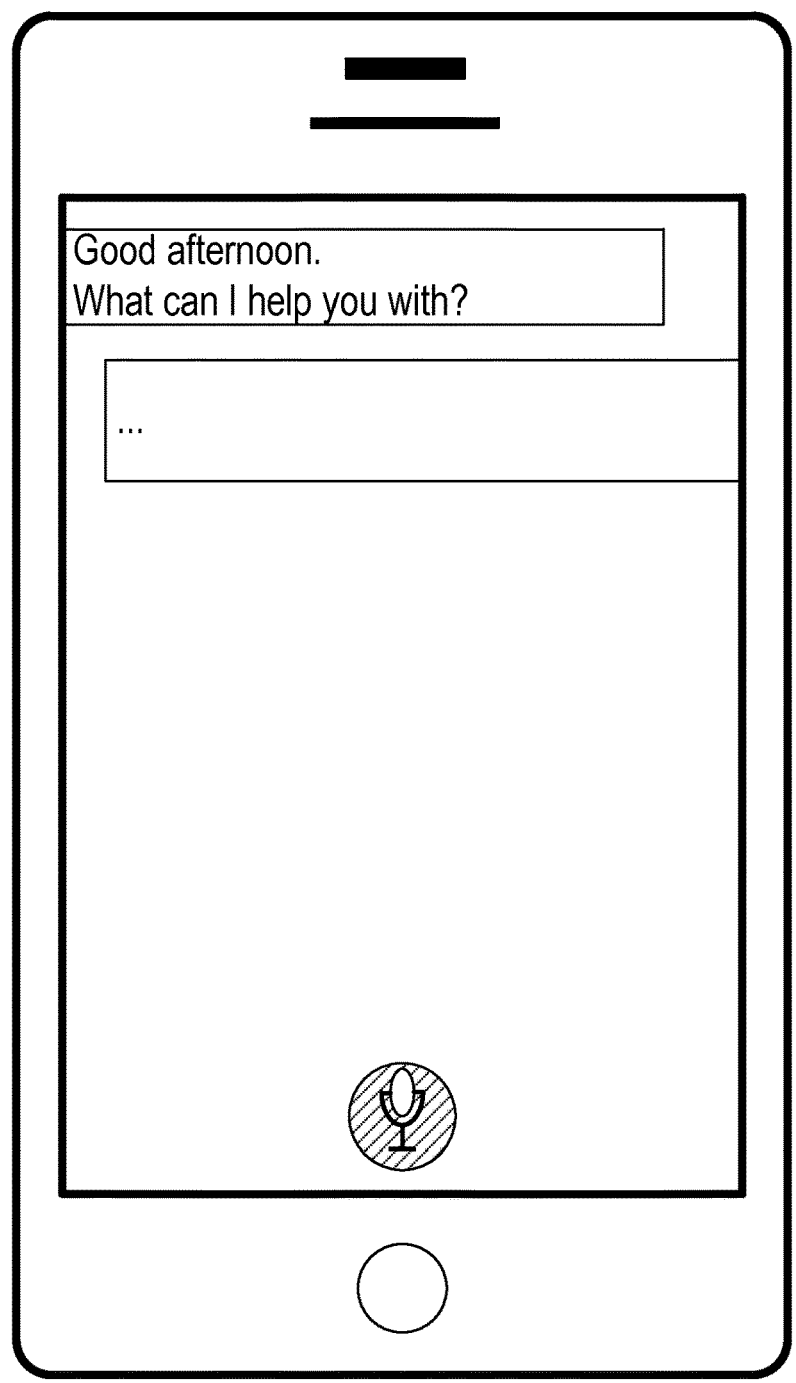
FIG. 3 illustrates an exemplary user interface for software in accordance with one or more preferred implementations.

FIG. 3 illustrates an exemplary user interface for software in accordance with one or more preferred implementations. A user can interact with the software by, for example, uttering the phrase "Show me all results for Peter Eastman". In response, the software processes the user's utterance and presents, to the user, all results for Peter N. Eastman, as illustrated in FIG. 4.

Figure 5:
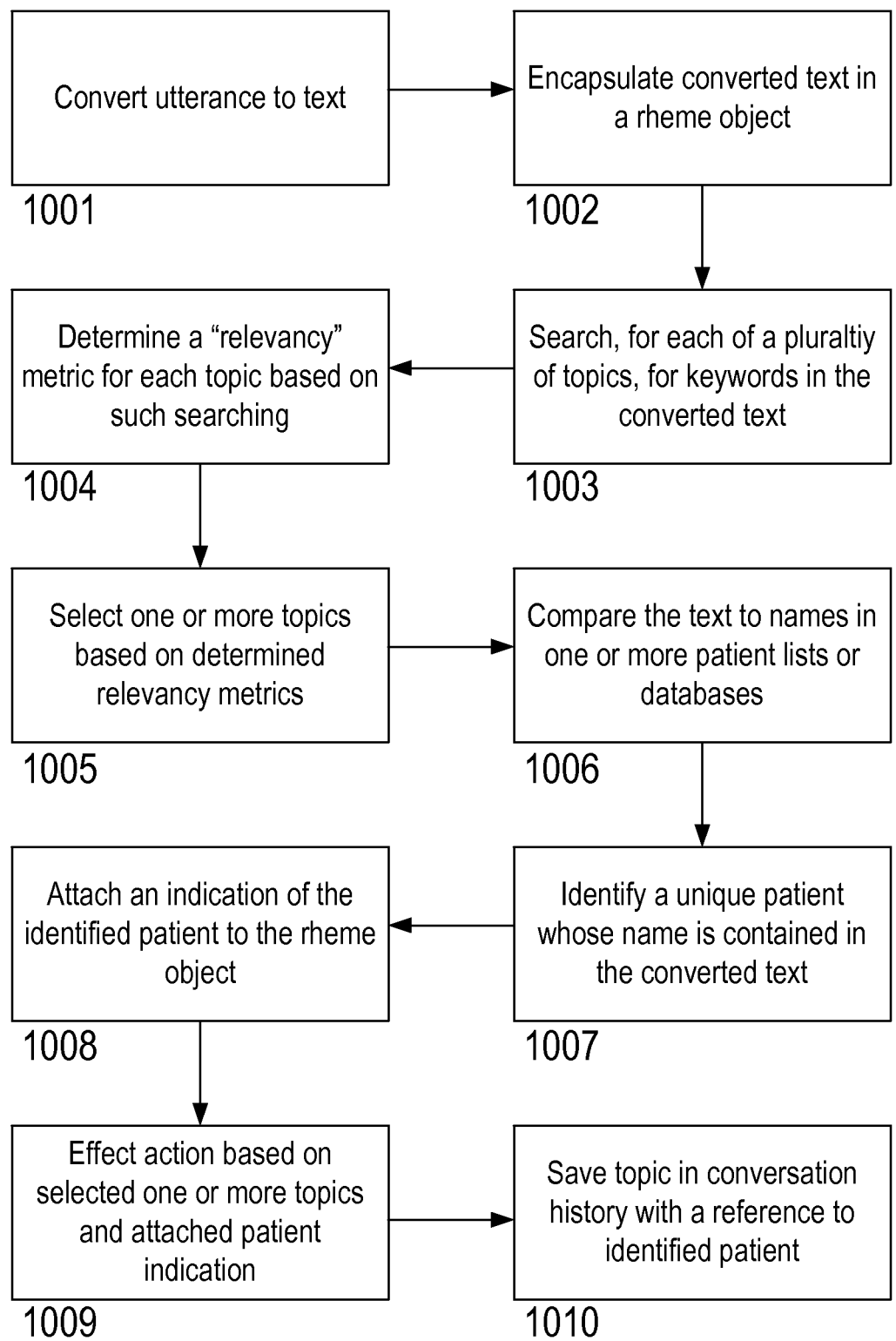
FIG. 5 illustrates an exemplary methodology for responding to a user's query.

An exemplary methodology for accomplishing this is illustrated in FIG. 5. This exemplary methodology includes converting the user's utterance to text at step 1001. encapsulating the converted text in a rheme object at step 1002, searching, for each of a plurality of topics, for keywords in the converted text at step 1003, determining a relevancy metric for each of the plurality of topics based on such searching at step 1004, selecting one or more topics based on determined relevancy metrics at step 1005, comparing some or all of the converted text to names in one or more patient lists or databases at step 1006, identifying a unique patient whose name is contained in the converted text at step 1007, attaching an indication of the identified patient to the rheme object at step 1008, effecting an action (in the exemplary case noted above, displaying results) based on the selected one or more topics and the attached patient indication at step 1009, and saving the topic in a conversation history with a reference to the identified patient at step 1010.

When a topic is selected, that topic saves a reference to the specified patient. The topic is then placed in a conversation history; this serves as context for the conversation. For example, when a new phrase is spoken by a user, the user preferably does not necessarily need to specify the patient name again. Preferably, if the user says something such as "How about orders?", the conversational agent will, upon failing to find a patient name in the new phrase, use the patient from the previous topic.

Figure 4:
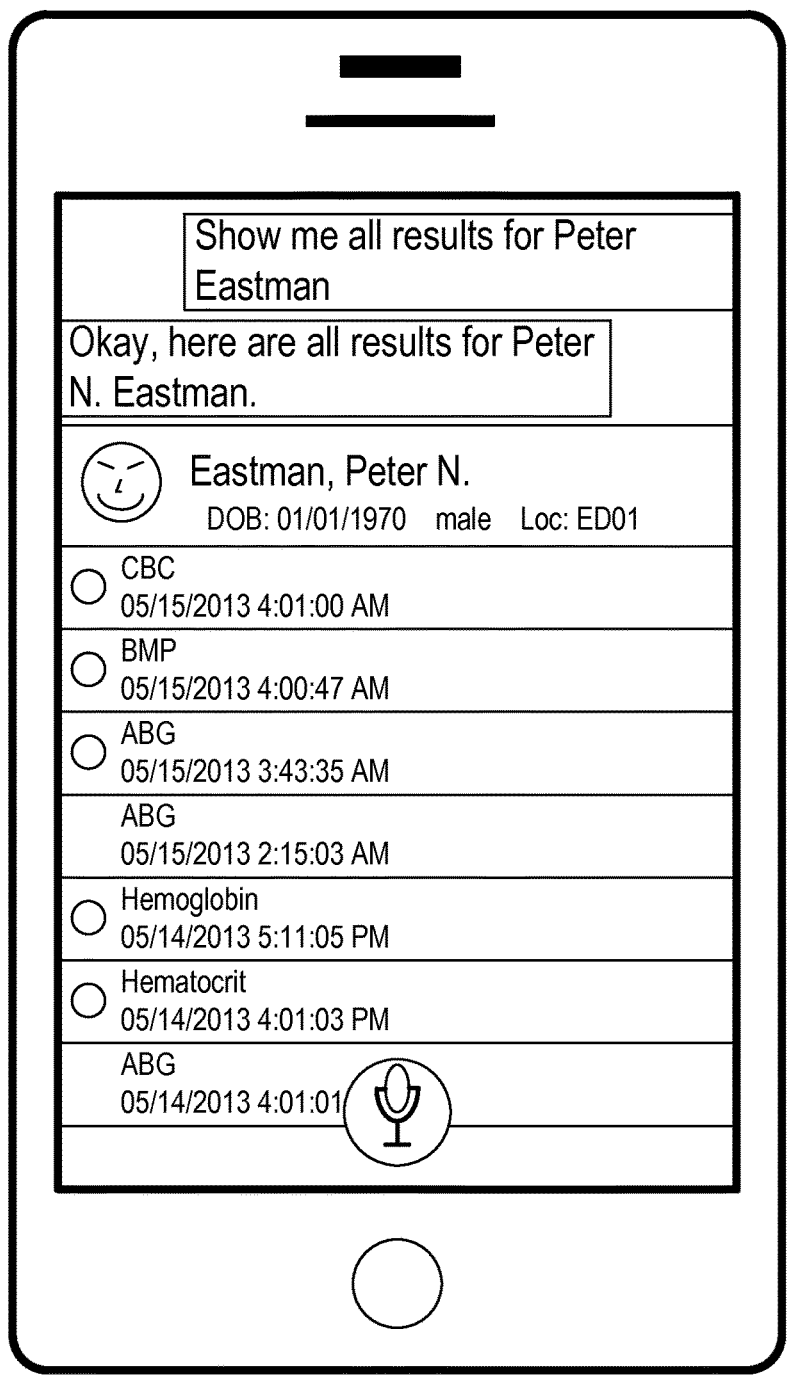
FIG. 4 illustrates presentation of results in response to a user's query for results.
Figure 6:
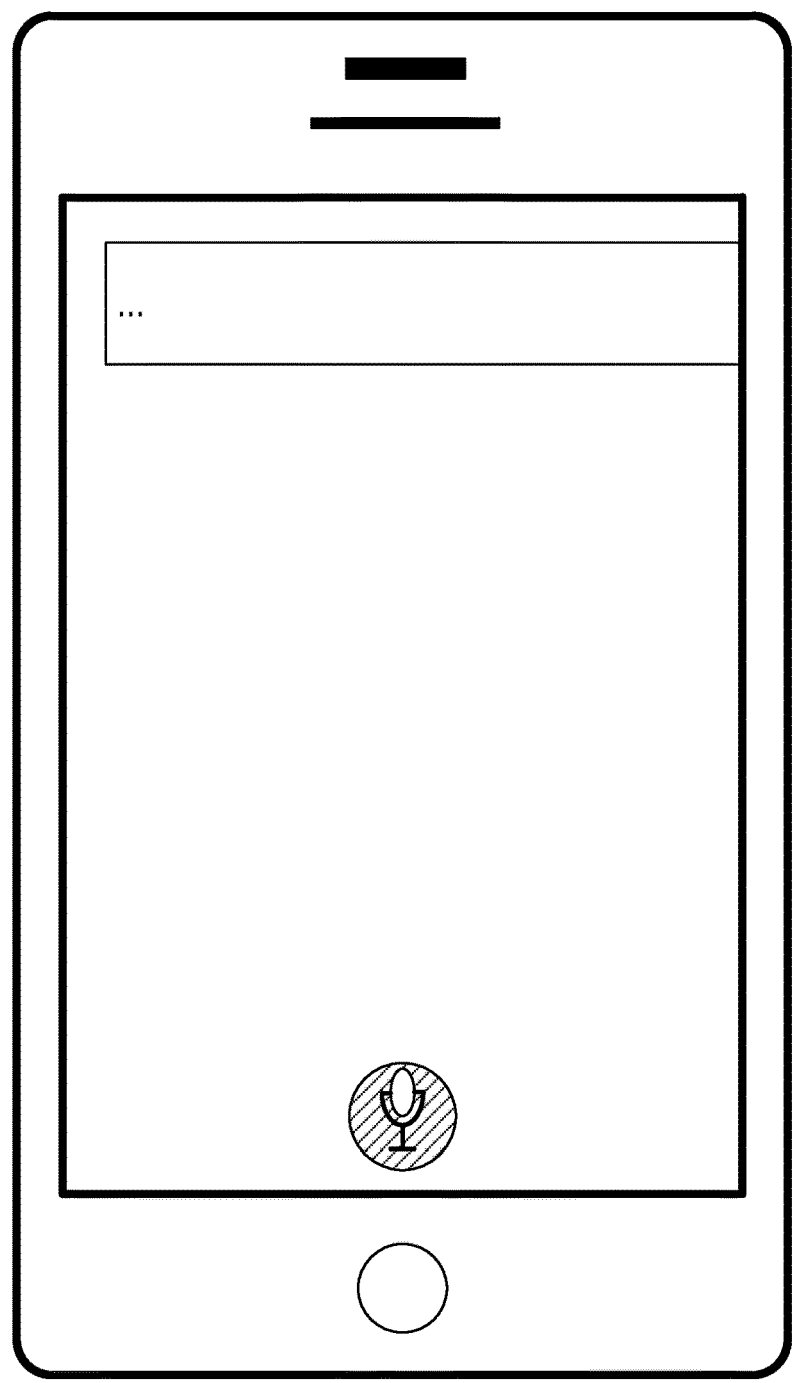
FIG. 6 illustrates a user query for abnormal results.
Figure 7:
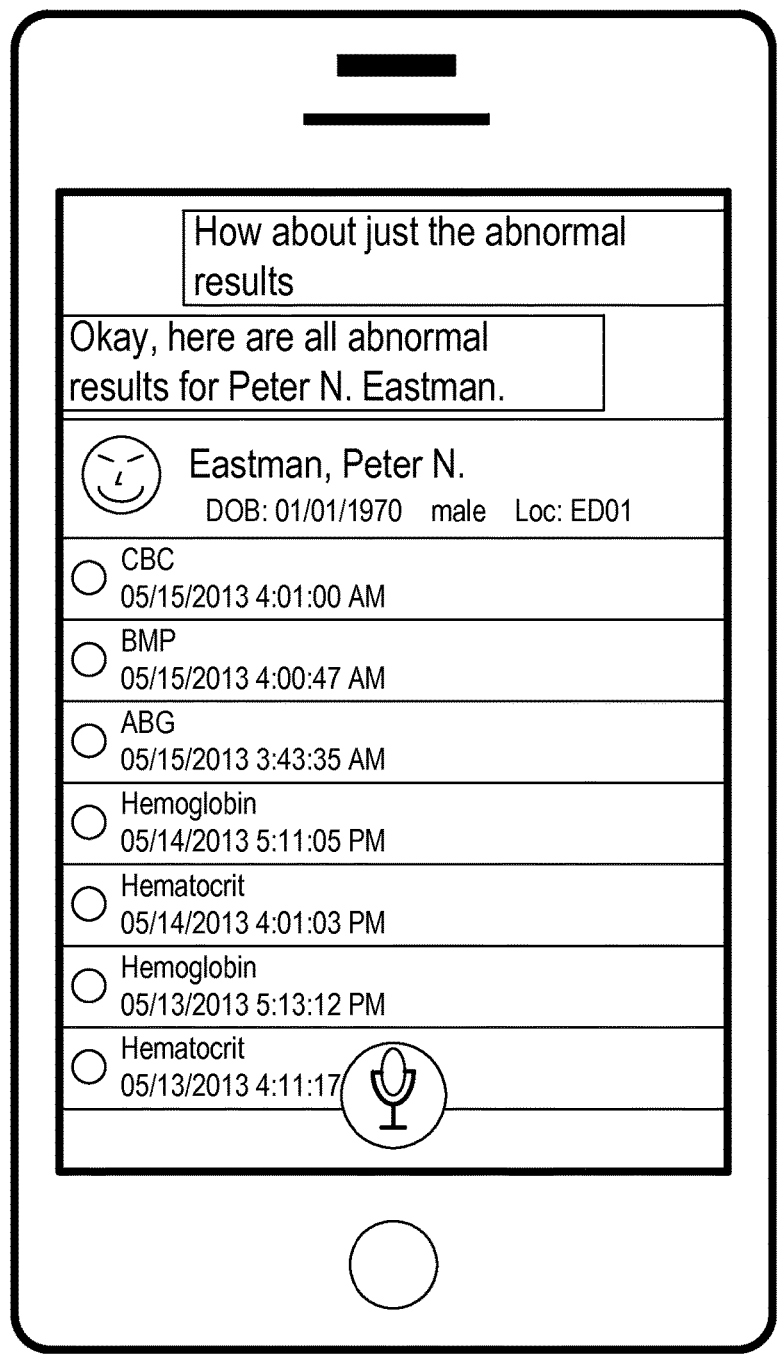
FIG. 7 illustrates the presentation of abnormal results in response to the query of FIG. 6.
Figure 8:
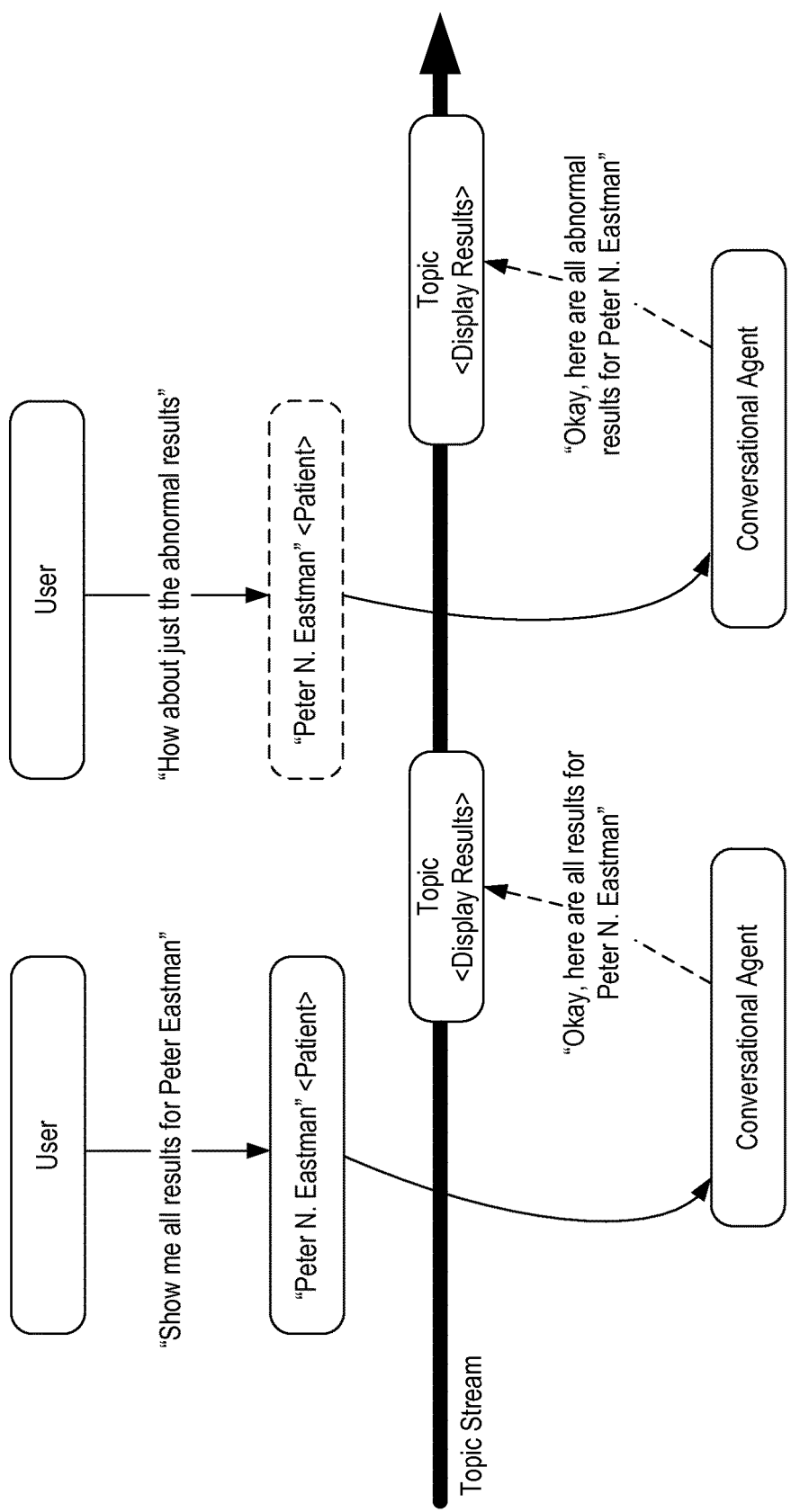
FIG. 8 illustrates the use of a previous reference to a patient as context for a subsequent utterance.
Figure 9:
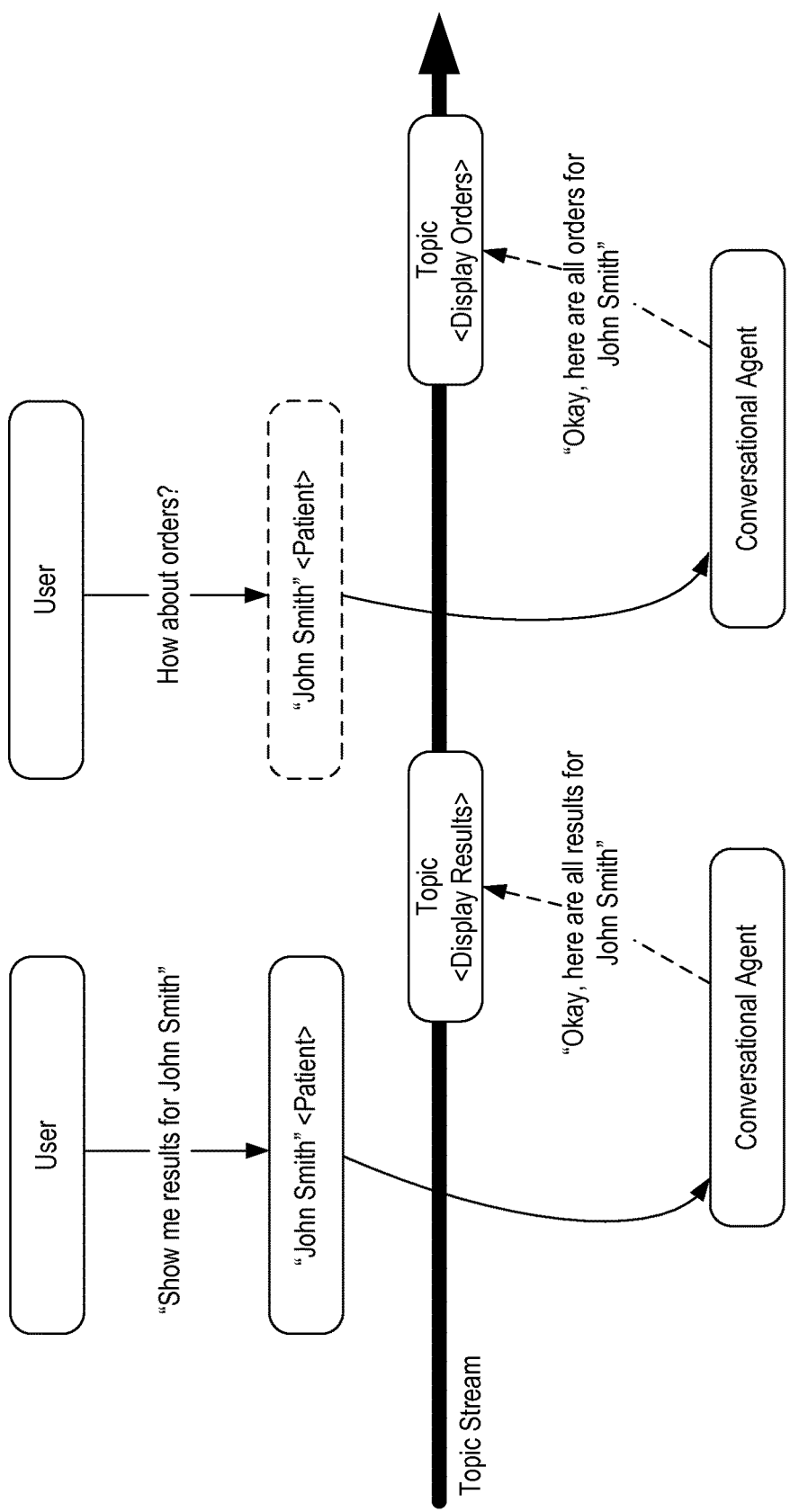
FIG. 9 illustrates the use of a previous reference to a patient for a first topic as context for an utterance corresponding to a second topic.

For example, returning to the example of FIGS. 3-4, thereafter, the user might further interact with the software by uttering the phrase "How about just the abnormal results", as illustrated in FIG. 6. In response, the software processes the user's utterance and presents, to the user, all results for Peter N. Eastman, as illustrated in FIG. 7. FIG. 8 illustrates the use of the previous reference to Peter Eastman as context for the subsequent utterance. FIG. 9 similarly illustrates the use of a previous reference to John Smith for a first topic as context for an utterance corresponding to a second topic.

Figure 10:
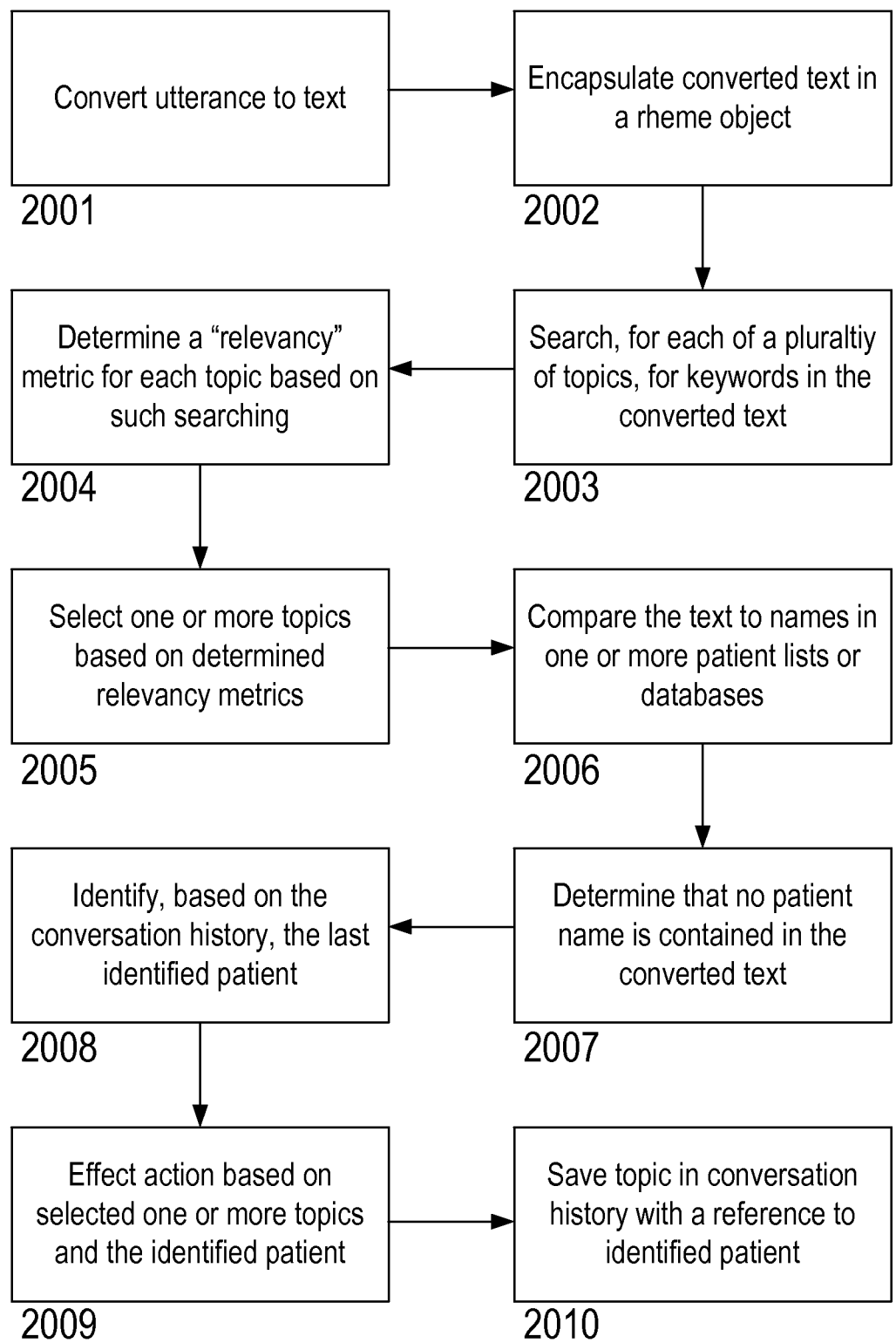
FIG. 10 illustrates an exemplary methodology for use of a previous reference to a patient as context for a subsequent utterance.

FIG. 10 illustrates an exemplary methodology for use of such a previous reference to a patient as context for a subsequent utterance. This exemplary methodology includes converting the user's utterance to text at step 2001, encapsulating the converted text in a rheme object at step 2002, searching, for each of a plurality of topics, for keywords in the converted text at step 2003, determining a relevancy metric for each of the plurality of topics based on such searching at step 2004, selecting one or more topics based on determined relevancy metrics at step 2005, comparing some or all of the converted text to names in one or more patient lists or databases at step 2006, determining that no patient name is contained in the converted text at step 2007, identifying, based on the conversation history, a last identified patient at step 2008, effecting an action based on the selected one or more topics and the identified patient at step 2009, and saving the topic in a conversation history with a reference to the identified patient at step 2010.

Figure 11:
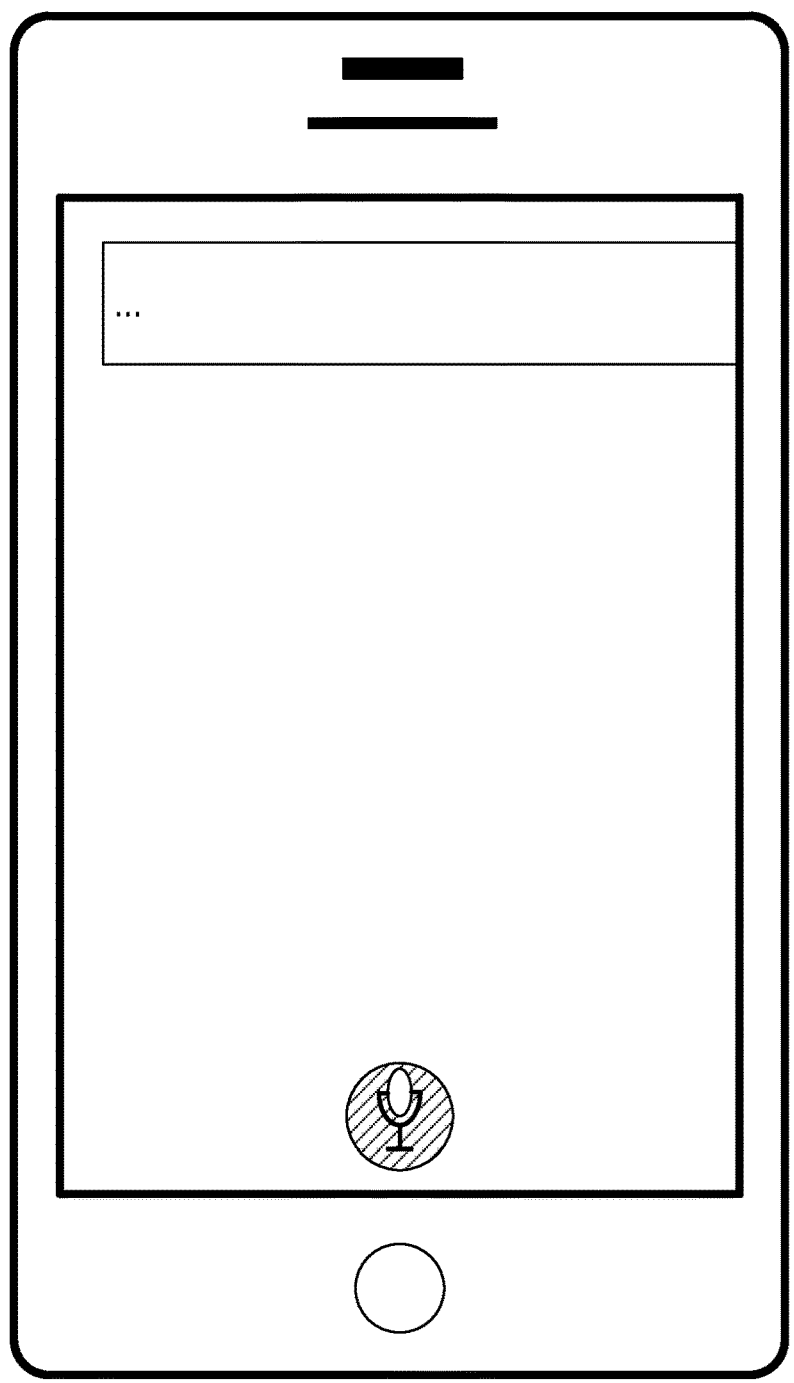
FIG. 11 illustrates a user query for information regarding another patient.

A user can also change the patient while still on the same topic; in this way they can apply the same data search to a different patient. For example, returning to the example of FIG. 7, thereafter, the user might further interact with the software by uttering the phrase "Now how about for Sally Smith", as illustrated in FIG. 11.

Figure 12:
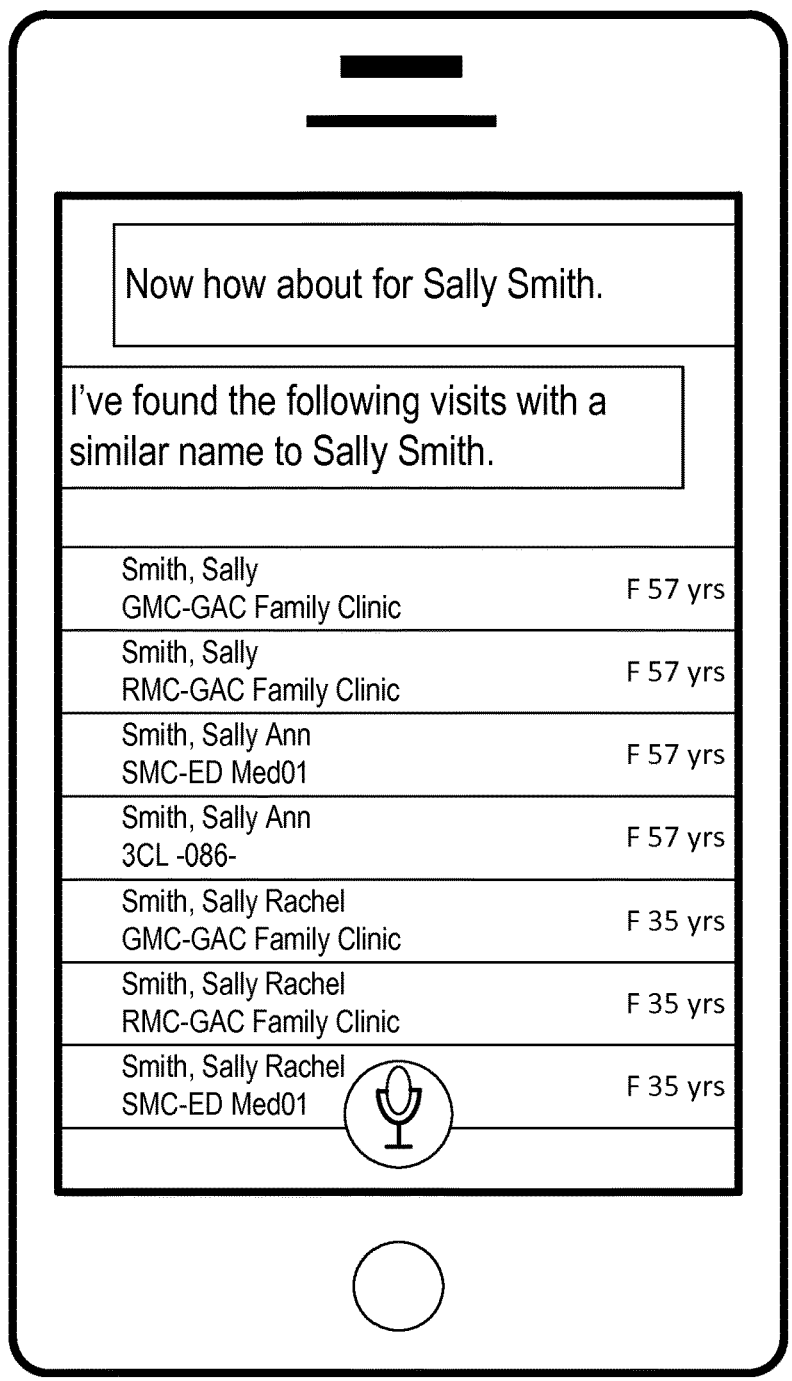
FIG. 12 illustrates an exemplary interface for disambiguation accessed following the user query illustrated in FIG. 11.
Figure 13:
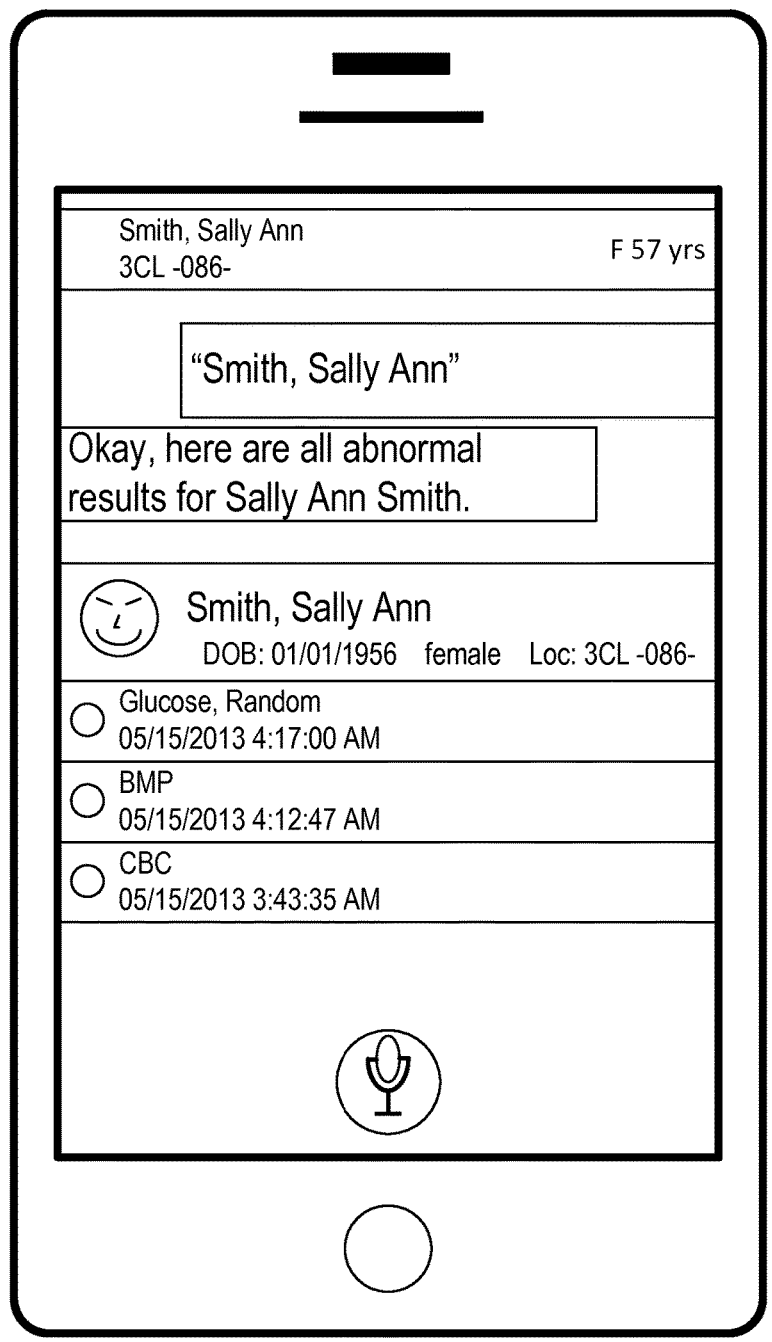
FIG. 13 illustrates presentation of results in response to the user query in FIG. 11.

In one or more preferred implementations, if there are multiple patients with the same name, or a user's utterance is unclear or ambiguous, then the user is preferably provided information about a plurality of patients and asked to disambiguate which patient they were referring to by selecting a particular patient via touchscreen, voice, or other input. FIG. 12 illustrates an exemplary such interface for disambiguation accessed following the user's utterance illustrated in FIG. 11. Upon selection by the user of a particular patient or visit, the software continues processing the user's utterance and presents, to the user, all results for Sally Smith, as illustrated in FIG. 13.

Figure 14:
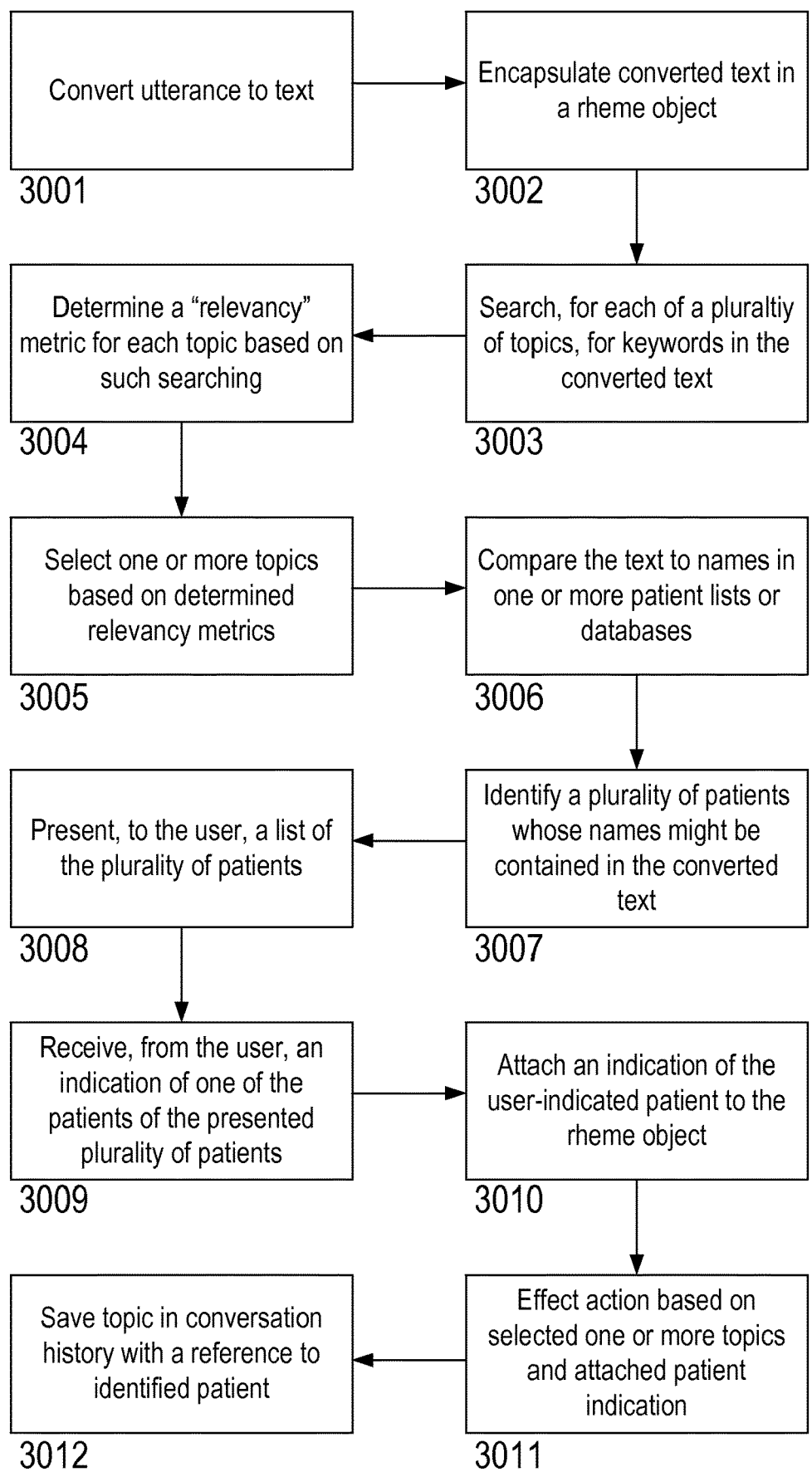
FIG. 14 illustrates an exemplary methodology involving disambiguation.

An exemplary methodology for accomplishing this is illustrated in FIG. 14. This exemplary methodology includes converting the user's utterance to text at step 3001, encapsulating the converted text in a rheme object at step 3002, searching, for each of a plurality of topics, for keywords in the converted text at step 3003, determining a relevancy metric for each of the plurality of topics based on such searching at step 3004, selecting one or more topics based on determined relevancy metrics at step 3005, comparing some or all of the converted text to names in one or more patient lists or databases at step 3006, identifying a plurality of patients or visits that might correspond to the converted text at step 3007, presenting, to the user, a list of the plurality of patients or visits at step 3008, attaching an indication of the identified patient to the rheme object at step 3009, effecting an action based on the selected one or more topics and the attached patient indication at step 3010, and saving the topic in a conversation history with a reference to the identified patient at step 3011.

Just as the software preferably saves context related to a recently searched patient, in one or more preferred implementations, the software preferably additionally saves context with respect to a previously utilized topic and allows a user to look up the same information for another patient via an utterance of that patient's name. For example, a user could simply utter "Now how about for Jane Smith".

Figure 15:
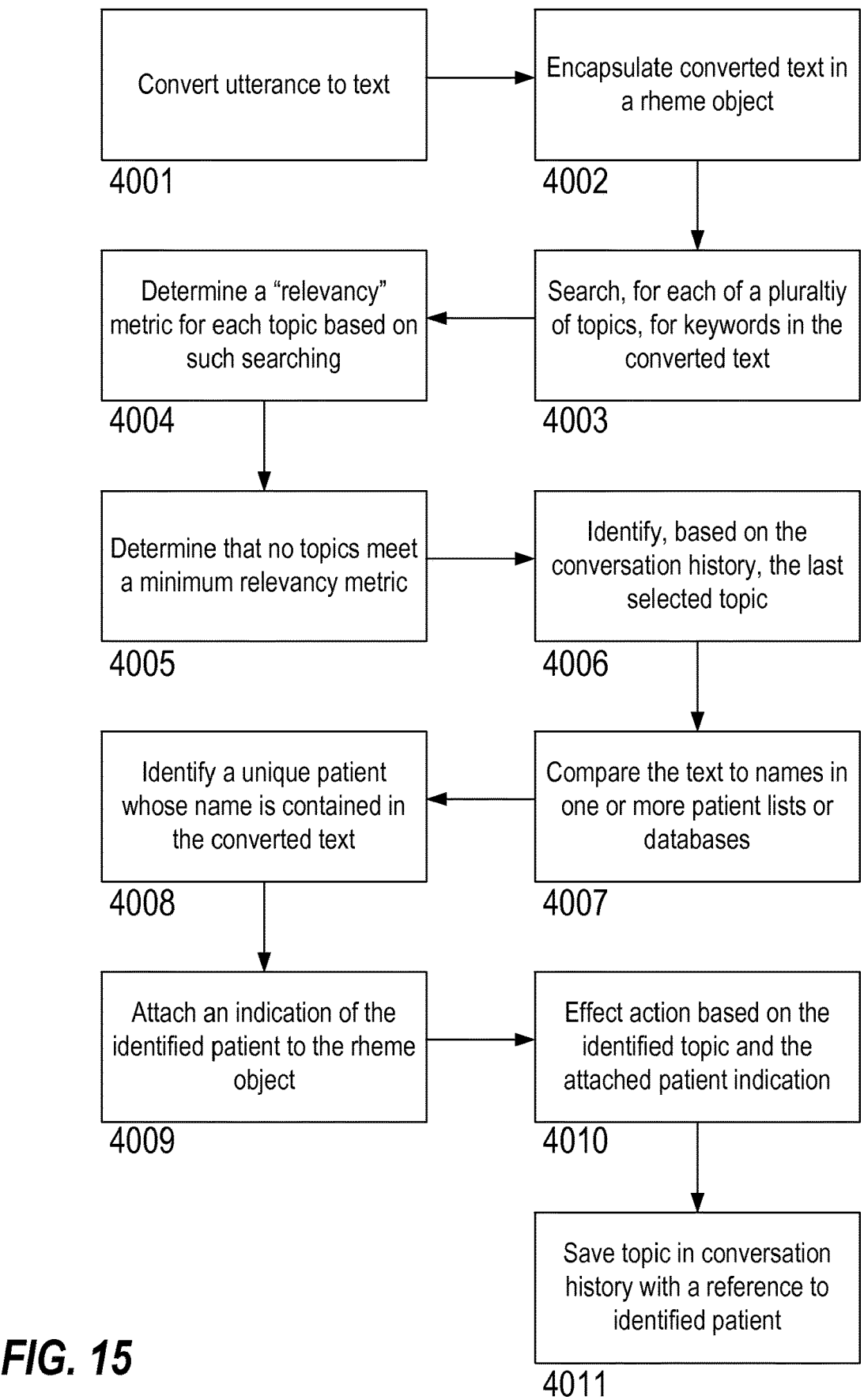
FIG. 15 illustrates an exemplary methodology for utilizing context with respect to a previously utilized topic.

An exemplary methodology for accomplishing this is illustrated in FIG. 15. This exemplary methodology includes converting the user's utterance to text at step 4001, encapsulating the converted text in a rheme object at step 4002, searching, for each of a plurality of topics, for keywords in the converted text at step 4003, determining a relevancy metric for each of the plurality of topics based on such searching at step 4004, determining that no topics meet a minimum relevancy metric at step 4005, identifying, based on a conversation history, the last selected topic at step 4006, comparing the converted text to names in one or more patient lists or databases at step 4007, identifying a unique patient whose name is contained in the converted text at step 4008, attaching an indication of the identified patient to the rheme object at step 4009, effecting an action (in the exemplary case noted above, displaying results) based on the selected one or more topics and the attached patient indication at step 4010, and saving the topic in a conversation history with a reference to the identified patient at step 4011.

Figure 16:
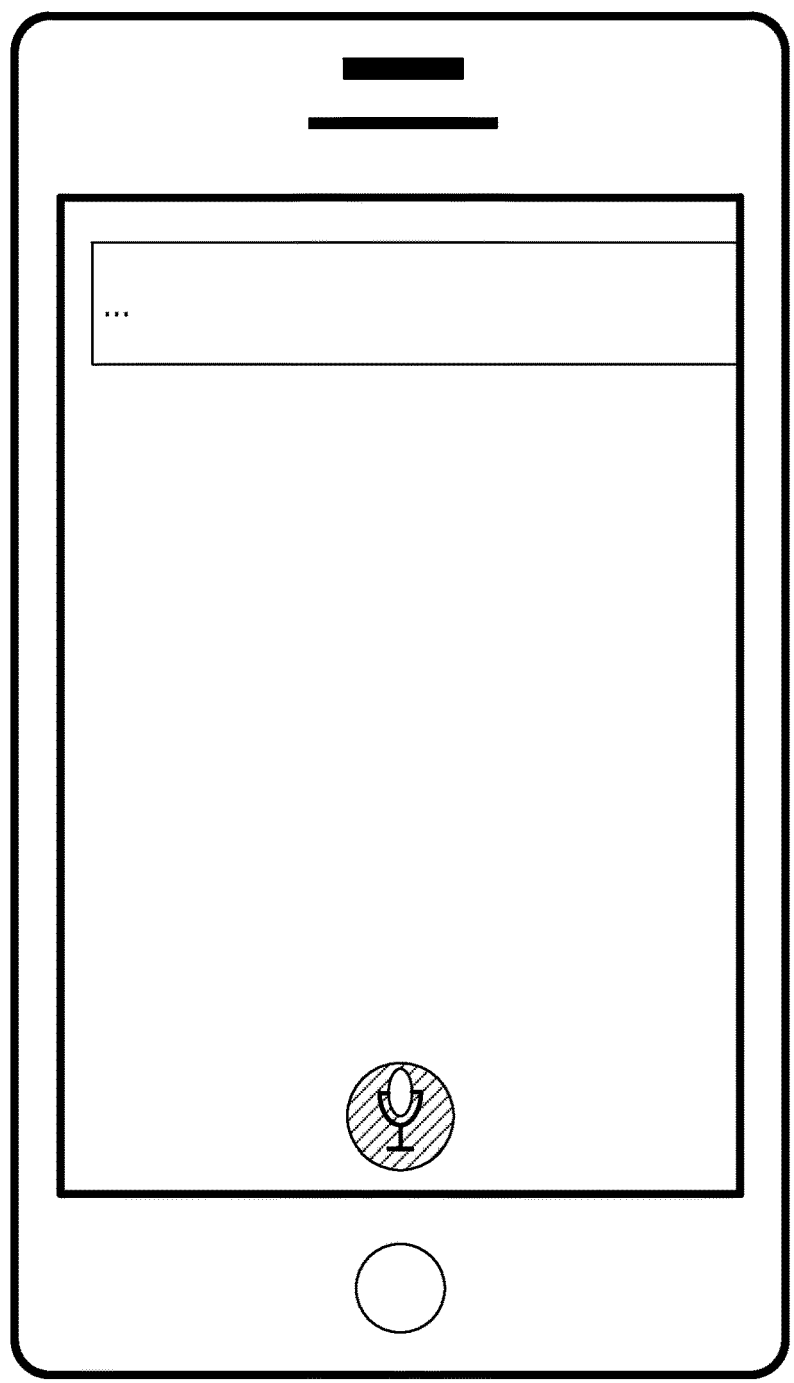
FIGS. 16-17 illustrate prompting of a user for the name of a patient for which the user would like to view allergy information.
Figure 17:
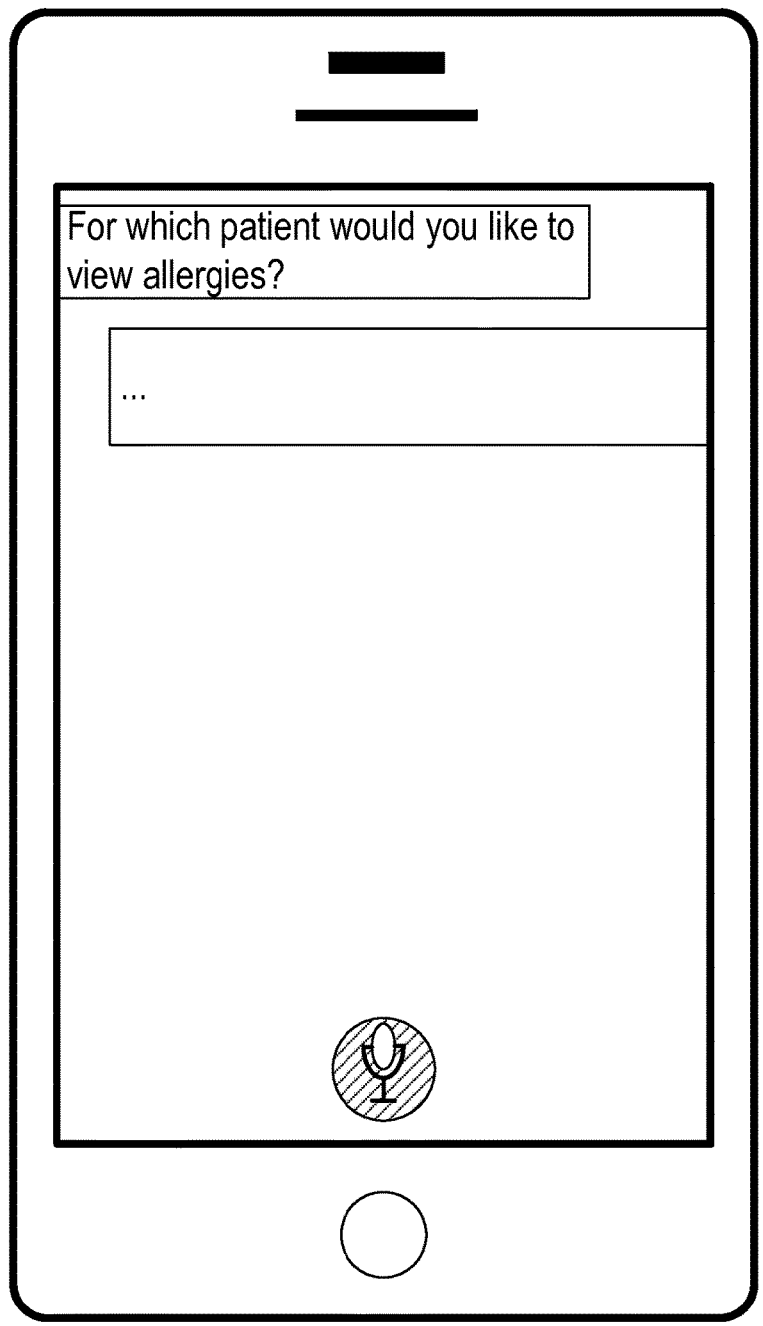

Notably, if there is no context available, the software may instead prompt a user to provide additional information. For example, FIGS. 16-17 illustrate prompting of a user for the name of a patient for which the user would like to view allergy information.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A processor-based method for operating an electronic device configured to function as an agent for a user interface in a medical environment utilizing conversation histories, the method comprising:
   (a) receiving, via microphone of an electronic device, a first utterance from a user corresponding to a first spoken command identifying a first patient;
   (b) converting, utilizing one or more processors, the first utterance to first text;
   (c) encapsulating, utilizing one or more processors, the converted first text in a first rheme object;
   (d) searching, for each of a plurality of topics utilizing one or more processors, for keywords in the converted first text;
   (e) determining, utilizing one or more processors, a relevancy metric for each of the plurality of topics based on the keyword searching of the converted first text;
   (f) selecting, utilizing one or more processors, one or more topics as a first set of one or more relevant topics based on the determined relevancy metrics;
   (g) comparing, utilizing one or more processors, some or all of the converted first text to names in one or more patient lists or databases;
   (h) determining, utilizing one or more processors based on comparing some or all of the converted first text, that the first utterance included an identification of the first patient based on successful matching during the comparing of some or all of the converted first text;
   (i) based on the determination that the first utterance included an identification of the first patient, attaching, utilizing one or more processors, an indication of the identified first patient to the rheme object;
   (j) displaying, to the user via a display device associated with the electronic device, first information associated with the first patient based on the selected first set of one or more relevant topics and the identified first patient;
   (k) saving, utilizing one or more processors, the selected first set of one or more relevant topics in a conversation history in association with the identified first patient;
   (l) receiving, via the microphone of the electronic device, a second utterance corresponding to a second spoken command, the second spoken command not including an identification of a patient;
   (m) converting, utilizing one or more processors, the second utterance to second text;
   (n) encapsulating, utilizing one or more processors, the converted second text in a second rheme object;
   (o) searching, for each of a plurality of topics utilizing one or more processors, for keywords in the converted second text;
   (p) determining, utilizing one or more processors, a relevancy metric for each of the plurality of topics based on the keyword searching of the converted second text;
   (q) selecting, utilizing one or more processors, one or more topics as a second set of one or more relevant topics based on the determined relevancy metrics;
   (r) comparing, utilizing one or more processors, some or all of the converted second text to names in the one or more patient lists or databases;
   (s) determining, utilizing one or more processors based on comparing some or all of the converted second text, that the second utterance did not include an identification of a patient, and, based thereon, attaching an indication of the previously identified first patient to the rheme object;
   (t) generating and displaying, to the user via the display device associated with the electronic device, second information associated with the first patient based on the selected second set of one or more relevant topics and the previous identification of the first patient; and
   (u) saving, utilizing one or more processors, the selected second set of one or more relevant topics in a conversation history in association with the previously identified first patient.

2. The processor-based method of claim 1, wherein converting, utilizing one or more processors, the first utterance to first text is performed at or from the electronic device.

3. The processor-based method of claim 1, wherein converting, utilizing one or more processors, the first utterance to first text is performed remote from the electronic device.

4. The processor-based method of claim 1, wherein converting, utilizing one or more processors, the first utterance to first text is performed at a first server remote from the electronic device.

5. The processor-based method of claim 1, wherein encapsulating, utilizing one or more processors, the converted first text in a first rheme object is performed at the first server.

6. The processor-based method of claim 1, wherein encapsulating, utilizing one or more processors, the converted first text in a first rheme object is performed at a second server.

7. The processor-based method of claim 1, wherein each of the determined relevancy metrics comprises a numerical score.

8. A processor-based method for operating an electronic device configured to function as an agent for a user interface in a medical environment utilizing conversation histories, the method comprising:
   (a) receiving, via a microphone of an electronic device, an utterance corresponding to a spoken command, the spoken command identifying a first patient;
   (b) converting, utilizing one or more processors, the utterance to text;
   (c) encapsulating, utilizing one or more processors, the converted text in a rheme object;
   (d) searching, for each of a plurality of topics utilizing one or more processors, for keywords in the converted text;
   (e) determining, utilizing one or more processors, a relevancy metric for each of the plurality of topics based on the keyword searching;
   (f) selecting, utilizing one or more processors, one or more topics as one or more relevant topics based on the determined relevancy metrics;
   (g) comparing, utilizing one or more processors, some or all of the converted text to names in one or more patient lists or databases;
   (h) determining, based on such comparing, that the utterance included an identification of the first patient based on successful matching during the comparing of some or all of the converted first text;
   (i) attaching, utilizing one or more processors, an indication of the identified first patient to the rheme object;
   (j) generating and displaying, to the user via a display device associated with the electronic device, information associated with the first patient based on the selected one or more topics and the identified first patient.

9. A processor-based method for operating an electronic device configured to function as an agent for a user interface in a medical environment utilizing conversation histories, the method comprising:
- converting, via one or more processors, a user's utterance to text;
- encapsulating, via the one or more processors, the converted text in a rheme object;
- searching, via the one or more processors, for each of a plurality of topics for keywords in the converted text;
- determining, via the one or more processors, a relevancy metric for each of the plurality of topics based on such searching;
- selecting, via the one or more processors, one or more topics based on determined relevancy metrics meeting or exceeding a predetermined relevancy metric;
- comparing, via the one or more processors, some or all of the converted text to names in one or more patient lists or databases;
- identifying, via the one or more processors, a unique patient whose name is contained in the converted text;
- attaching, via the one or more processors, an indication of the identified patient to the rheme object;
- executing, via the one or more processors, an action based on the selected one or more topics and the attached patient indication; and
- saving the topic in a conversation history with a reference to the identified patient.

* * * * *